United States Patent
Daum

(10) Patent No.: US 6,908,468 B2
(45) Date of Patent: Jun. 21, 2005

(54) DEVICES FOR NUCLEAR SPIN TOMOGRAPHY MAGNETIC RESONANCE IMAGING (MRI)

(75) Inventor: Wolfgang Daum, Groton, MA (US)

(73) Assignee: MRI Devices Daum GmbH, Schwerin (DE)

( * ) Notice: Subject to any disclaimer, the term of this patent is extended or adjusted under 35 U.S.C. 154(b) by 0 days.

(21) Appl. No.: 10/080,436

(22) Filed: Feb. 22, 2002

(65) Prior Publication Data

US 2002/0155025 A1 Oct. 24, 2002

(30) Foreign Application Priority Data

Feb. 22, 2001 (DE) .......................................... 101 08 581

(51) Int. Cl.$^7$ .......................... A61B 17/56; A61B 17/58
(52) U.S. Cl. .......................... 606/76; 600/433; 600/434; 600/435; 600/436; 623/1.1; 420/585; 420/586.1; 148/442
(58) Field of Search ............................... 420/585, 586.1, 420/442; 623/1.1; 606/76; 600/433–436, 585; 148/442

(56) References Cited

U.S. PATENT DOCUMENTS

| | | | | |
|---|---|---|---|---|
| 3,620,852 A | * | 11/1971 | Herchenroeder et al. ... | 148/557 |
| 3,767,385 A | * | 10/1973 | Slaney ........................ | 420/585 |
| 4,657,019 A | * | 4/1987 | Walsh et al. ................. | 606/153 |
| 4,931,255 A | * | 6/1990 | Doherty et al. ............. | 420/586 |
| 5,190,832 A | * | 3/1993 | Ogawa et al. ............... | 428/678 |
| 5,226,980 A | * | 7/1993 | Tsukuta et al. ............. | 148/419 |
| 5,424,744 A | * | 6/1995 | Westphal ...................... | 342/27 |
| 5,636,641 A | * | 6/1997 | Fariabi ........................ | 600/585 |

FOREIGN PATENT DOCUMENTS

| | | | | |
|---|---|---|---|---|
| JP | 55-82739 | * | 6/1980 | ................. 420/585 |
| JP | 60-9848 | * | 1/1985 | ................. 420/439 |

* cited by examiner

*Primary Examiner*—John P Sheehan
(74) *Attorney, Agent, or Firm*—Saliwanchik, Lloyd & Saliwanchik

(57) ABSTRACT

The subject invention relates to a material for magnetic resonance imaging, and apparatus incorporating such material. The subject material can comprise cobalt, nickel, and chromium and can be used in nuclear spin tomography MRI. In specific embodiments, the subject material can be used in stents, mechanical springs, and guide wires.

15 Claims, No Drawings

DEVICES FOR NUCLEAR SPIN TOMOGRAPHY MAGNETIC RESONANCE IMAGING (MRI)

CROSS-REFERENCE TO RELATED APPLICATION

This application claims priority to German Application No. 10108581.8, filed Feb. 22, 2001.

BACKGROUND OF INVENTION

In today's interventional nuclear spin tomography MRI, it is desirable to utilize materials of a certain elasticity, such as is used in springs, in biopsy and other automated needles, and cardiovascular or other cavity stents. Titanium based materials exhibiting low field distortion, or image artifacts, in nuclear spin tomography, are in part too brittle and have insufficient elasticity. Filigree structures imaging isn't optimal either.

BRIEF SUMMARY OF THE INVENTION

The subject invention pertains to devices for use in nuclear spin tomography magnetic resonance imaging (MRI). The subject devices incorporate materials having desirable properties, such as elasticity. In a specific embodiment, the subject device can incorporate stainless steels of a cobalt-nickel chrome-based alloy. The subject invention relates to devices for nuclear spin tomography MRI, such as springs, automated needles, stents, cardiovascular stents, torsion springs, coil springs, membrances, and guide wires.

DETAILED DESCRIPTION OF THE INVENTION

The subject invention pertains to devices for use in nuclear spin tomography magnetic resonance imaging (MRI). The subject devices incorporate materials having desirable properties, such as elasticity. In a specific embodiment, the subject device can incorporate stainless steels of a cobalt-nickel chrome-based alloy. The subject invention relates to devices for nuclear spin tomography MRI, such as springs, automated needles, stents, cardiovascular stents, torsion springs, coil springs, membrances, and guide wires.

The first alloy on a CoNiCr base consists of 42 to 48% cobalt by weight, 19 to 25% nickel by weight, 16 to 20% chromium by weight, 2–6% molybdenum by weight, 2–6% tungsten by weight, 2.5 to 7.5% iron by weight, and titanium and beryllium for the balance. The material can be further hardened. It is breakproof and can be utilized for highly challenged small dimensional springs, which must also be antimagnetic.

The material is highly suitable for springs utilized in measuring and display instruments of all kinds, including torsion and coil springs, membranes and other springs requiring high resistance accuracy. It is equally suitable for stents. For this application it is drawn into tiny tubes and subsequently cut into stents. Stents are metallic spring elements that are inserted into cavities in the human body, e.g., cardiovascular vessels, in order to prevent them from closing. The stents are introduced into the body with the help of catheters that are in turn guided in by guide wires. The core of the guide wire frequently consists of a long spring wire and the material cited here is ideally suited for its manufacture.

The material exhibits a high degree of corrosion resistance. Its superior cold fabrication properties in conjunction with good temperability produces an exceptionally durable, fatigue-free substance, that in tempered condition offers very attractive long-term stability values in situations with both high and low metal fatigue windows. Furthermore, the alloy can be utilized in a permanent application up to the middle temperature range, i.e., from −50° C. to 350° C. The material has an elasticity modulus of 219.5 to 234.4 kN/mm$^2$. Due its relative permeability of <1.005$\mu$ it cannot become magnetized in the nuclear spin tomography MRI or nuclear magnetic resonance unit. The material is biocompatible and can be used for implants in the human body.

Another material consists of 39 to 41% cobalt by weight, 15 to 18% nickel by weight, 19 to 21% chromium by weight, 6.5 to 7.5% molybdenum by weight, <0.15% carbon, <1.2% silicon by weight, <0.01% beryllium by weight, <0.015% sulfur by weight, <0.015% phosphorous by weight, and iron for the balance. The mechanical properties are similar to those of the first named materials, wherein the elasticity modulus (Youngs modulus) is at 212 kN/mm$^2$.

The materials are classified under the ISO 5832/7, AFNOR NR S 90-403, ASTM F1058-91 standards, where ISO 5832/7 is a material, as known in the art, having a chemical composition of 39 to 42% (m/m) cobalt, 18.5 to 21.5% (m/m) manganese, up to 1% (m/m) silicon, up to 0.15% (m/m) carbon, up to 0.015% (m/m) phosphorous, up to 0.015% (m/m) sulfur, up to 0.001% (m/m) beryllium, and iron for the balance.

What is claimed is:

1. A device comprising:
    cobalt-nickel-chromium-based alloy, wherein the cobalt-nickel-chromium-based alloy has the following composition:
        42% to 48% cobalt by weight; 19% to 25% nickel by weight; 16% to 20% chromium by weight; 2% to 6% molybdenum by weight; 2% to 6% tungsten by weight; 2.7% to 7.5% iron by weight; and titanium and beryllium for the balance, wherein the device is selected from the group consisting of: a stent, a spring, a needle, and a guide wire.
2. The device according to claim 1, wherein the device is a cardiovascular stent.
3. The device according to claim 1, wherein the device is a coil spring.
4. The device according to claim 1, wherein the device is a torsion spring.
5. The device according to claim 1, wherein the device is a biopsy needle.
6. The device according to claim 1, wherein the device consists essentially entirely of the cobalt-nickel-chromium-based alloy.
7. A method of treating a patient, comprising:
    inserting a stent into a cavity of a patient, wherein the stent comprises a cobalt-nickel-chromium-based alloy, wherein the cobalt-nickel-chromium-based alloy has the following composition:
        42% to 48% cobalt by weight; 19% to 25% nickel by weight; 16% to 20% chromium by weight; 2% to 6% molybdenum by weight; 2% to 6% tungsten by weight; 2.7% to 7.5% iron by weight; and titanium and beryllium for the balance.
8. The method according to claim 7, wherein inserting a stent into a cavity of a patient comprises inserting a stent into a cavity of a patient under nuclear spin tomography magnetic resonance imaging.

9. The method according to claim 7,
wherein the stent is a cardiovascular stent.

10. The method according to claim 7,
wherein the stent consists essentially entirely of the cobalt-nickel-chromium-based alloy.

11. The method according to claim 9,
wherein inserting a stent into a cavity of a patient comprises inserting the stent into a cardiovascular vessel of the patient.

12. A method of treating a patient, comprising:

inserting a stent into a cavity of a patient, wherein the stent comprises a cobalt-nickel-chromium-based alloy, wherein the cobalt-nickel-chromium-based alloy has the following composition: 39% to 41% cobalt by weight; 15% to 18% nickel by weight; 19% to 21% chromium by weight; 6.5% to 7.5% molybdenum by weight; up to 0.15% carbon by weight; up to 1.2% silicon by weight; up to 0.01% beryllium by weight; up to 0.015% sulfur by weight; up to 0.015% phosphorous by weight; and iron for the balance, wherein inserting a stent into a cavity of a patient comprises inserting a stent into a cavity of a patient under nuclear spin tomography magnetic resonance imaging.

13. The method according to claim 12,
wherein the stent is a cardiovascular stent.

14. The method according to claim 12,
wherein the stent consists essentially entirely of the cobalt-nickel-chromium-based alloy.

15. The method according to claim 13, wherein inserting a stent into a cavity of a patient comprises inserting the stent into a cardiovascular vessel of the patient.

* * * * *

UNITED STATES PATENT AND TRADEMARK OFFICE
CERTIFICATE OF CORRECTION

PATENT NO. : 6,908,468 B2  Page 1 of 1
APPLICATION NO. : 10/080436
DATED : June 21, 2005
INVENTOR(S) : Wolfgang Daum and Axel Winkel It is certified that error appears in the above-identified patent and that said Letters Patent is hereby corrected as shown below:

<u>Title Page, Item (75),</u>
"Inventor: Wolfgang Daum, Groton, MA (US)" should read --Inventors: Wolfgang Daum, Groton, MA (US); Axel Winkel, Schwerin (DE)--.

<u>Column 2,</u>
Line 23, "AFNOR NR" should read --AFNOR NF--.

<u>Column 2,</u>
Line 26, "21.5 % (m/m) manganese," should read --21.5% (m/m) chromium, 14-18% (m/m) nickel, 6.5 to 8% (m/m) molybdenum, 1 to 2.5% (m/m) manganese--.

<u>Column 2,</u>
Line 32, "cobalt-nickel" should read --a cobalt-nickel--.

Signed and Sealed this

Twenty-ninth Day of January, 2008

JON W. DUDAS
*Director of the United States Patent and Trademark Office*